(12) United States Patent
Yost et al.

(10) Patent No.: US 6,773,407 B2
(45) Date of Patent: Aug. 10, 2004

(54) NON-INVASIVE METHOD OF DETERMINING ABSOLUTE INTRACRANIAL PRESSURE

(75) Inventors: William T. Yost, Newport News, VA (US); John H. Cantrell, Jr., Williamsburg, VA (US); Alan E. Hargens, San Diego, CA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 91 days.

(21) Appl. No.: 10/263,286

(22) Filed: Sep. 25, 2002

(65) Prior Publication Data

US 2003/0191411 A1 Oct. 9, 2003

Related U.S. Application Data

(60) Provisional application No. 60/371,601, filed on Apr. 8, 2002.

(51) Int. Cl.[7] .................................. A61B 5/00
(52) U.S. Cl. ..................... 600/561; 600/300; 600/438
(58) Field of Search ............................. 600/300, 301, 600/438, 451, 485, 561

(56) References Cited

U.S. PATENT DOCUMENTS

| | | | |
|---|---|---|---|
| 4,841,986 A | * | 6/1989 | Marchbanks ............... 600/559 |
| 4,971,061 A | | 11/1990 | Kageyama et al. |
| 5,214,955 A | | 6/1993 | Yost et al. |
| 5,388,583 A | | 2/1995 | Ragauskas et al. |
| 5,591,476 A | | 1/1997 | Capodieci |
| 5,617,873 A | * | 4/1997 | Yost et al. ................... 600/561 |
| 5,919,144 A | * | 7/1999 | Bridger et al. .............. 600/561 |
| 6,117,089 A | | 9/2000 | Sinha |
| 6,210,346 B1 | | 4/2001 | Hall et al. |
| 6,231,509 B1 | | 5/2001 | Johnson et al. |
| 6,264,611 B1 | | 7/2001 | Ishikawa et al. |
| 6,387,051 B1 | * | 5/2002 | Ragauskas et al. ......... 600/438 |
| 6,413,227 B1 | | 7/2002 | Yost et al. |
| 6,475,147 B1 | | 11/2002 | Yost et al. |
| 2003/0171693 A1 | | 9/2003 | Yost et al. |
| 2003/0191409 A1 | | 10/2003 | Yost et al. |
| 2003/0191410 A1 | | 10/2003 | Yost et al. |

OTHER PUBLICATIONS

Toshiaki Ueno et al., "Effects of Whole Body Tilting on Intracranial Pressure Dynamics,".
Toshiaki Ueno et al., "Noninvasive Measurement of Pulsatile Intracranial Pressure Using Ultrasound," Acta Neurochir, p. 66–69, (Dec. 23, 1998).

* cited by examiner

Primary Examiner—Robert L. Nasser
Assistant Examiner—Patricia Mallari
(74) Attorney, Agent, or Firm—Helen M. Galus

(57) ABSTRACT

A method is presented for determining absolute intracranial pressure (ICP) in a patient. Skull expansion is monitored while changes in ICP are induced. The patient's blood pressure is measured when skull expansion is approximately zero. The measured blood pressure is indicative of a reference ICP value. Subsequently, the method causes a known change in ICP and measures the change in skull expansion associated therewith. The absolute ICP is a function of the reference ICP value, the known change in ICP and its associated change in skull expansion, and a measured change in skull expansion.

37 Claims, 2 Drawing Sheets

NON-INVASIVE METHOD OF DETERMINING ABSOLUTE INTRACRANIAL PRESSURE

CLAIM OF BENEFIT OF PROVISIONAL APPLICATION

Pursuant to 35 U.S.C. Section 119, the benefit of priority from provisional application 60/371,601, with a filing date of Apr. 8, 2002, is claimed for this non-provisional application.

ORIGIN OF THE INVENTION

The invention described herein was made by employees of the United States Government and may be manufactured and used by or for the Government for governmental purposes without the payment of any royalties thereon or therefor.

CROSS-REFERENCE TO RELATED APPLICATIONS

This patent application is co-pending with one related patent application entitled "NON-INVASIVE METHOD OF DETERMINING DIASTOLIC INTRACRANIAL PRESSURE" (NASA Case No. LAR 16440-1), by the same inventors as this patent application.

BACKGROUND OF THE INVENTION

1. Field of the Invention

This invention relates to determination of intracranial pressure. More specifically, the invention is a non-invasive method for determining the absolute intracranial pressure in a patient.

2. Description of the Related Art

The human brain and the spinal cord are immersed in a fluid called the cerebrospinal fluid (CSF) which is continuously generated and reabsorbed by the body. The CSF is contained in a membrane covering the inside of the skull and the spinal cord which terminates in a sack located at the sacrum. The brain and the membrane containing the CSF also contain blood vessels, which are in direct communication with the CSF and add to the total volume of the cerebrospinal system. The blood volume in these blood vessels varies rhythmically with the heartbeat thereby causing corresponding oscillations in the intracranial pressure (ICP). An accurate regulating process in the brain normally controls generation and reabsorption of CSF as well as the blood volume in the brain to maintain a constant ICP average value of about 40 mmHg. However, ICP changes when the regulating process is disturbed by, for example, tumors in the brain or trauma to the brain. Unfortunately, as little as 10 mmHg increase above average value in the ICP can cause insidious damage to the brain.

Given the above, monitoring ICP is of significant diagnostic and post-operative importance for patients with cranial injuries, pathologies or other conditions that may affect the pressure of the subarachnoidal fluid around the brain, and for patients who have undergone brain surgery. ICP has traditionally been measured and monitored by means of a pressure sensor inserted through the skull into the brain. Usually a hole is drilled in the skull and a catheter with a pressure sensor is inserted into the brain fluid. This known procedure, while simple and accurate is not suitable for long-term monitoring because an open wound must be maintained in the skull. Antibiotics are only partially effective in treating cranial infections so the pressure sensor typically can only be left in place for two weeks or less.

Long-term monitoring of ICP is currently achieved by implanting a pressure sensor and transmitter into the brain. The ICP is thereafter monitored by means of a receiver located outside the skull. However, this solution is not preferred because it includes the risks associated with implanting anything in the brain, and because of the problems of providing power to an implanted transmitter.

A variety of non-invasive systems and/or methods of measuring relative changes in ICP have been described in each of U.S. patent application Ser. Nos. 09/459,384, 09/493,044, 10/094,023, and 10/121,932. However, none of these provide for the measurement or determination of an absolute ICP. U.S. Pat. No. 5,617,873 discloses a method and system for monitoring absolute ICP, but requires the use of two known changes in the volume of CSF while recording corresponding changes in ICP by means of a calibrated measurement device.

SUMMARY OF THE INVENTION

Accordingly, it is an object of the present invention to provide a method of determining absolute ICP in a non-invasive fashion.

Another object of the present invention is to provide a method of determining absolute ICP that minimizes the number of procedures used.

Other objects and advantages of the present invention will become more obvious hereinafter in the specification and drawings.

In accordance with the present invention, a method is presented for determining absolute intracranial pressure (ICP) in a patient. In at least one embodiment, skull expansion of the patient is monitored as a function of time while changes in ICP in the patient are induced. Blood pressure of the patient is then measured at a time when skull expansion is approximately zero. The measured blood pressure at this time is indicative of a reference ICP value. A known change in ICP in the patient is caused after the time of zero skull expansion. A change in skull expansion associated with this known change in ICP is then measured. The absolute ICP is a function of the reference ICP value, the known change in ICP and the change in skull expansion associated with the known change in ICP.

DETAILED DESCRIPTION OF THE INVENTION

Figure 1:
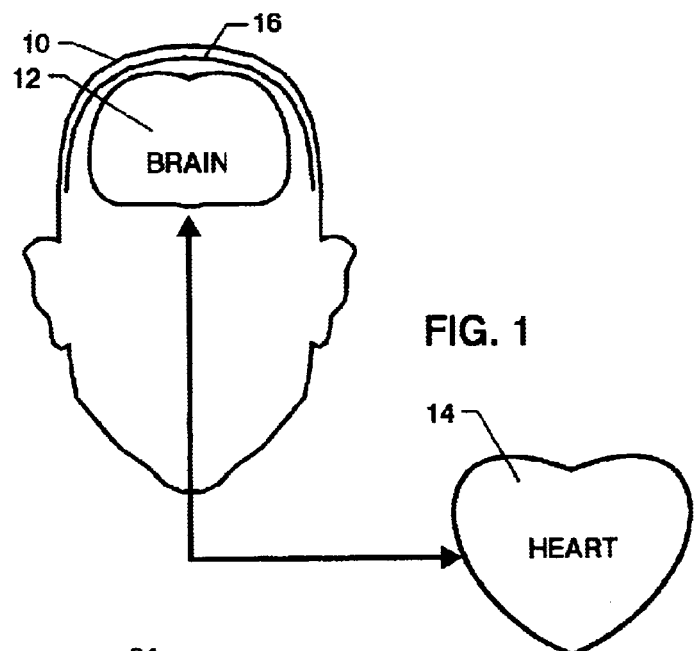
FIG. 1 is a schematic view of the skull and brain of a patient with the brain being coupled to the patient's heart.

Referring now to the drawings, and more particularly to FIG. 1, a patient's skull 10 is illustrated with his brain referenced by numeral 12. As is well known, brain 12 is a venous structure that is coupled to the patient's heart 14 and, therefore, undergoes systolic-diastolic changes in blood pressure. The blood pressure in the venous bed of the brain is known as venous bed pressure and will be referenced herein as $P_{VB}$. Surrounding brain 12 is the patient's cerebrospinal fluid (CSF) 16, the pressure of which is known as intracranial pressure or ICP as it will be referenced herein.

Skull 10 tends to expand and contract with changes in ICP. However, the compliance (i.e., the ability of skull 10 to expand with increasing ICP) of skull 10 is not sufficient to accommodate the pressure regulation needed for proper circulation of blood within brain 12 and the patient's CSF system (not shown). Accordingly, pressure within skull 10 is controlled by compliance of the brain's venous bed in association with the addition/removal of CSF 16. The determination and/or continuous monitoring of the absolute ICP of CSF 16 is important in determining whether or not a patient has a problem interfering with the body's natural ability to control ICP.

In terms of skull expansion, the present invention takes note of the fact that the venous bed pressure $P_{VB}$ will be equal to ICP when skull 10 is neither expanding nor contracting for a skull expansion of "zero." As is known in the art, venous bed pressure $P_{VB}$ can be determined from a standard arterial blood pressure measurement thereby making ICP easily determined at a time of zero skull expansion. Once ICP at zero skull expansion (or $ICP_{REF}$ as it will be referred to hereinafter) is determined, the present invention goes on to determine absolute ICP by measuring skull expansion changes brought about by associated known changes in ICP.

Before describing the details of a method of the present invention, it is to be understood that skull expansion measurements, the inducement of changes in ICP, and/or the measurement of changes in ICP, can be carried out in a variety of ways without departing from the scope of the present invention. For example, skull expansion can be measured/monitored by means of sophisticated micrometers (not shown) or by other non-invasive means such as the mechanical-acoustic system that will be described herein. The intentionally induced changes in ICP can be brought about by mechanical manipulation of the patient (e.g., pressure applied to the skull, through the use of a tilt bed, immersion of the patient in a negative pressure chamber, etc.) or by chemical manipulation of the patient (e.g., giving the patient drugs to: alter blood gas concentration, decrease production of CSF, increase the uptake rate of CSF, etc.). Measurement of changes in ICP can be measured/determined by a variety of acoustic systems (e.g., pulse-echo, pitch-catch, etc.) such as the constant frequency pulsed phase-locked-loop ultrasonic measuring system described in U.S. Pat. No. 5,214,955, which patent is incorporated herein by reference as if set forth in its entirety.

Figure 2:
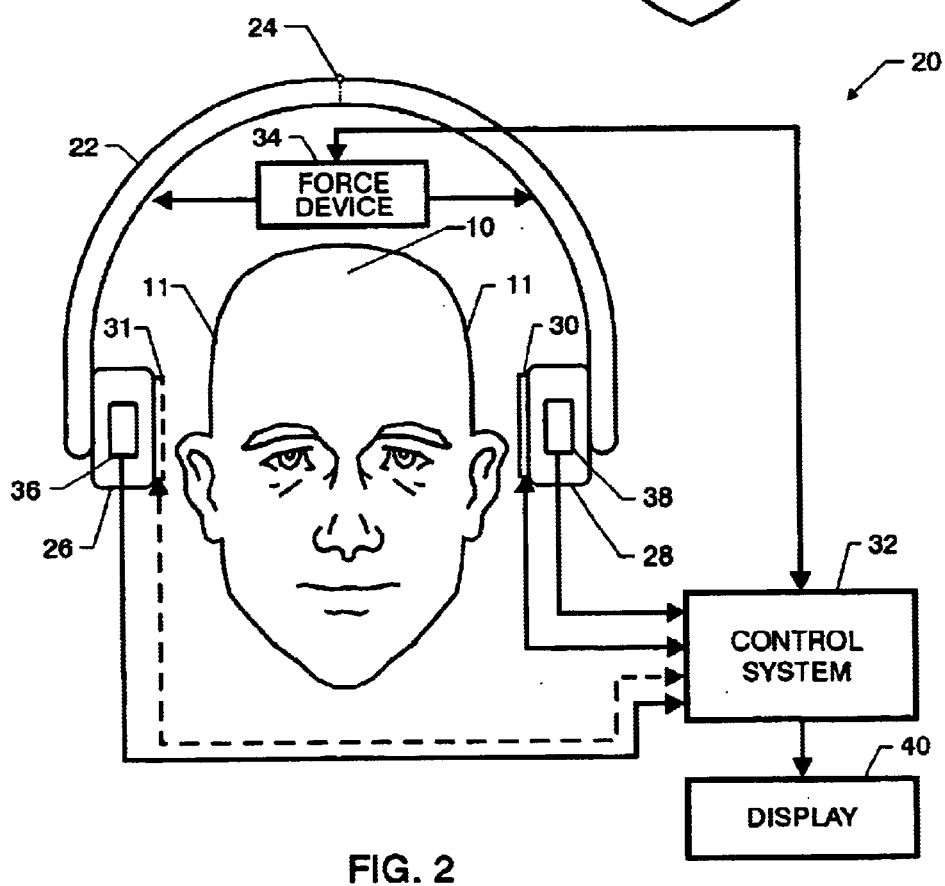
FIG. 2 is a schematic view of a system that can be used to measure/monitor skull expansion in a patient for use by a method of the present invention.

By way of a non-limiting example, FIG. 2 illustrates a system 20 that monitors skull expansion of a patient in order to determine when there is zero skull expansion. System 20 includes an adjustable headband 22 hinged at its central portion as indicated by dashed line 24. Pressure pads 26 and 28 are positioned at either end of headband 22 such that, when headband 22 is fitted over a patient's skull 10, pressure pads 26 and 28 are positioned at approximately diametrically opposed positions about skull 10. Each of pressure pads 26 and 28 can define a conforming pad (e.g., a gel-filled pad) to assure uniform contact with skin 11 adjacent skull 10.

Mounted to pressure pad 28 is a transducer 30 capable of transmitting and receiving acoustic signals for use in a pulse-echo measurement approach. Signals are provided to transducer 30 by a control system 32 and acoustic echoes received by transducer 30 are provided to control system 32.

In the pulse-echo approach, pressure pad 26 can be constructed as an anechoic chamber to reduce reflections from the skin-air interface adjacent the side of the skull subjected to the acoustic signals. Separate transmission and reception transducers could also be used for either pulse-echo or pitch-catch measurement approaches. For example, in terms of a pitch-catch measurement approach, transducer 30 could be a dedicated transmitter and a transducer 31 (shown in phantom) could be a dedicated receiver mounted on pad 26.

A force device 34 is coupled to headband 22 on either side of hinge 24. Force device 34 is any controllable device capable drawing headband 22 together about hinge 24 such that an increasing pressure is applied to skull 10 via each of pads 26 and 28. Examples of force device 34 can include, but are not limited to, solenoids, screw drives, hydraulic drives, gear drives, etc., where system response is linear. That is, force device 34 should preferably be "linear" in its expansion and contraction characteristics as it follows skull expansion. Such linearity is manifested by a force device having a constant (i.e., linear) and known stiffness (or modulus).

Control of force device 34 is maintained by control system 32 which can be entirely automatic or can include means for accepting manual inputs. To monitor the amount of pressure applied to skull 10, pressure sensors 36 and 38 can be provided at each of pressure pads 26 and 28, respectively. The pressure readings can be used by control system 32 as a feedback control for force device 34. Pressure outputs can also be displayed on a display 40.

To monitor skull expansion using the pulse-echo approach, headband 22 is placed on skull 10 such that pads 26 and 28 are in contact with the patient's skin 11 adjacent skull 10. With respect to pad 28, note that transducer 30, as well as portions of pad 28 to the sides of transducer 30, will contact skin 11. This insures good coupling of acoustic signals transmitted into skull 10 from transducer 30 as well as good coupling of acoustic signal reflections from skull 10 to transducer 30.

Prior to monitoring skull expansion using system 20, it may be desirable to establish and apply a differential pressure bias to skull 10 at each of the transmission, reception and, if applicable, reflection locations about skull 10 in order to reduce or eliminate the effects associated with pulsatile blood perfusion, i.e., the small amount of systolic-diastolic blood located between the patient's skin 11 and skull 10. The amount of differential pressure required to reduce or eliminate the influence of pulsatile blood perfusion can be determined by monitoring skull expansion as a function of applied differential pressures. Initially, the slope of a plot of these two parameters will be fairly steep. However, the slope will level off to a constant once the effects of pulsatile blood perfusion are reduced/eliminated. Note that this step is not required if acoustic signals can be coupled directly to/from the skull 10 as opposed to indirectly through the patient's skin 11.

Figure 3:
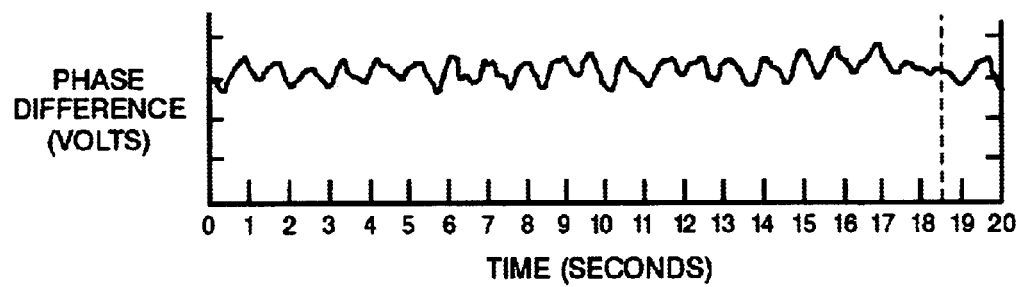
FIG. 3 is a graph of a patient's skull expansion versus time as measured by, for example, the system in FIG. 2.

In general, system 20 monitors skull expansion during a period of time that changes in ICP are induced in the patient. At the time when skull expansion is zero (or approximately so), the patient's venous bed pressure (or $P_{VB}$) will be equal to the patient's ICP. In accordance with the teachings of U.S. Pat. No. 5,214,955, system 20 measures phase difference between the acoustic signal transmitted into skull 10 and the acoustic signal measured at a detection location. As mentioned above, the detection location can be: i) the same as the transmission location when a single transmission/reception transducer 30 is used, ii) adjacent the transmission location if a dedicated reception transducer is mounted adjacent transducer 30, or iii) at another location that is spaced apart form the transmission location, e.g., at a location diametrically-opposed to the transmission location as would be the case if dedicated reception transducer 31 were used. Thus, in terms of system 20, zero (or approximately zero) skull expansion is indicated when the phase difference between the transmission and reception locations is approximately zero. For example, as illustrated in FIG. 3, when phase difference is measured by system 20 in terms of an output voltage, (approximately) zero skull expansion (i.e., (approximately) zero slope) occurs at approximately 18.5 seconds. Note that in tests of the present invention, the phase difference waveform depicted in FIG. 3 correlated well with an absolute ICP measurement that used an invasive probe.

During the time that skull expansion is being monitored, the patient can be "manipulated" to bring about changes in ICP. Such manipulations can be mechanical or chemical in nature. Mechanical manipulations can include the use of additional pressure being applied by force device 34 of system 20, the use of a tilt bed while system 20 maintains a differential pressure bias, the immersion of the patient in a negative pressure chamber, etc. Chemical manipulations include drug intervention techniques for increasing/decreasing ICP.

Figure 4:
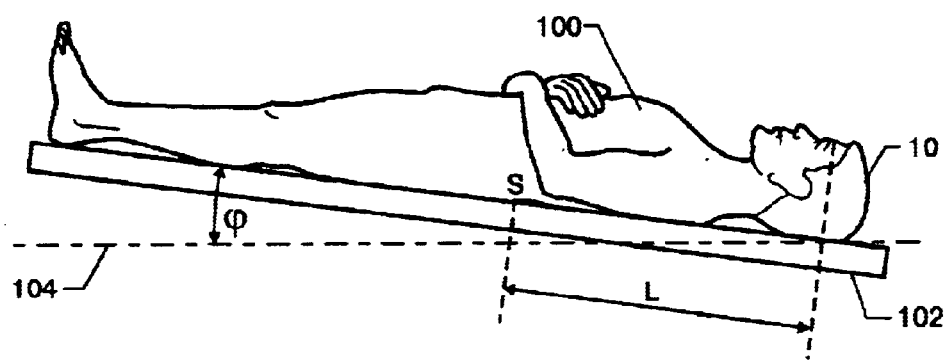
FIG. 4 is a side view of a patient lying in a supine position on a tiltable bed for mechanical manipulation of the patient as a means to induce/cause changes in intracranial pressure (ICP) in the patient.

At the time of zero skull expansion, venous bed pressure $P_{VB}$ of the patient's brain can be determined from a standard arterial blood pressure measurement. The value of $P_{VB}$ at this time is essentially equal to ICP which, as mentioned above, will be used as a reference value $ICP_{REF}$. From this point in time, known changes in ICP are brought about while corresponding changes in skull expansion are monitored. The causing of known changes in ICP can be brought about by the tilt bed/angle method, which has been described in U.S. Pat. No. 5,617,873, which patent is incorporated herein by reference. Briefly, as shown in FIG. 4, a patient 100 lies supine on a tiltable bed 102. Note that while a system, for example system 20, would remain coupled to patient 100, it has been omitted from FIG. 4 for clarity of illustration. With bed 102 tilted by an angle φ with the legs of patient 100 higher than skull 10, a change (increase in this case) in ICP (or ΔICP) can be given as $$\Delta ICP = \rho g L \sin\phi \quad (1)$$

where ρ is the mass density of spinal fluid, g is the earth's gravitational constant, L is the distance from the center of the patient's sacrum (the location of which is indicated at S) to the center of skull 10, and φ is the amount of tilt angle of bed 102 relative to a (horizontal) datum 104 used when determining $ICP_{REF}$. The present invention is not limited to a measurement of L that originates at the patient's sacrum. For example, L could be measured with respect to another reference point such as the point at which pressure in the spinal column does not change with tilt angle. Thus, for any given patient with a known/measurable distance L, ΔICP can be calculated using equation (1).

Changes in skull expansion measured by system 20 are essentially defined by changes in path length that the acoustic signal travels between its transmission and reception locations. That is, between any two measurement points in time, the path length "l" that the acoustic signal travels gets longer in the case of positive skull expansion or shorter in the case of negative skull expansion (i.e., skull contraction). Path length l could be defined by one or more paths across skull 10 depending on the number of such lengths traversed by the acoustic signal between its transmission and reception locations. Thus, the change in path length between any two points in time is "Δl."

The change in path length, Δl, for the change in ICP, ΔICP, can be measured by system 20. The two values can be used to determine the skull expansion calibration factor, K, by, $$K = \Delta ICP / \Delta l \quad (2)$$

For any measured path length change, $\Delta l_M$, where, $$\Delta l_M = l_M - l_{REF}, \quad (3)$$

The absolute ICP or $ICP_{ABS}$ is given as $$ICP_{ABS} = ICP_{REF} + K(\Delta l_M) \quad (4)$$

The advantages of the present invention are numerous. Absolute ICP is determined through the use of easily taken measurements. The process is non-invasive in nature and can, therefore, be used for both one-time and longer term monitoring scenarios. Thus, the present invention will find great utility in both critical and non-critical ICP-related pathologies as well as other medical applications requiring knowledge of absolute ICP.

Although the invention has been described relative to a specific embodiment thereof, there are numerous variations and modifications that will be readily apparent to those skilled in the art in light of the above teachings. For example, rather than using the tilt bed approach to causing known changes in ICP, system 20 could be used to apply incremental increases in headband pressure to bring about changes in skull dimensions. The changes in skull dimensions can then be used to infer changes in ICP resulting from skull expansion/contraction. It is therefore to be understood that, within the scope of the appended claims, the invention may be practiced other than as specifically described.

What is claimed as new and desired to be secured by Letters Patent of the United States is:

1. A method of determining absolute intracranial pressure (ICP) in a patient, comprising the steps of:

monitoring skull expansion of the patient as a function of time;

inducing changes in ICP in the patient;

measuring blood pressure of the patient at a time when said skull expansion is approximately zero during said step of inducing wherein said blood pressure at said time is indicative of a reference ICP value;

causing a known change in ICP in the patient after said time;

measuring a change in said skull expansion of the patient associated with said known change in ICP; and determining a skull expansion calibration factor, wherein the absolute ICP is a function of said reference ICP value, said measured change in skull expansion and said skull expansion calibration factor.

2. A method according to claim 1 wherein each of said steps of monitoring said skull expansion and measuring said change in said skull expansion comprises the steps of:

coupling an acoustic signal to a first location on the patient's skin adjacent the skull of the patient;

detecting said acoustic signal at a second location on the patient's skin adjacent the skull of the patient; and measuring a phase difference between said acoustic signal so-coupled at said first location and said acoustic signal so-detected at said second location, wherein said phase difference is indicative of said skull expansion.

3. A method according to claim 2 further comprising the step of applying pressure to the patient's skin at each of said first location and said second location prior to said steps of coupling and detecting, wherein pulsatile blood perfusion at said first location and said second location is reduced.

4. A method according to claim 2 wherein said first location and said second location are approximately diametrically-opposed to one another on either side of the skull of the patient.

5. A method according to claim 2 wherein said first location and said second location are approximately the same location.

6. A method according to claim 1 wherein said step of inducing comprises the step of manipulating the patient in a mechanical fashion.

7. A method according to claim 1 wherein said step of inducing comprises the step of manipulating the patient in a chemical fashion.

8. A method according to claim 1 wherein said step of causing comprises the step of manipulating the patient in a mechancal fashion.

9. A method according to claim 1 wherein said step of causing comprises the step of manipulating the patient in a chemical fashion.

10. A method of determining absolute ICP in a patient, comprising the steps of:
    monitoring skull expansion of the patient as a function of time, wherein said skull expansion is defined in terms of a length l of a path traversing at least a portion of the skull of the patient;
    inducing changes in ICP in the patient;
    measuring blood pressure of the patient at a time when said skull expansion is approximately zero during said step of inducing wherein said blood pressure at said time is indicative of a venous bed pressure of the patient, and wherein said venous bed pressure at said time is equal to a reference ICP value $ICP_{REF}$;
    causing a known change $\Delta ICP$ in ICP in the patient after said time;
    measuring a change $\Delta l$ in said path associated with said known change in ICP; and
    determining a skull expansion calibration factor, wherein the absolute ICP is equal to $$ICP_{REF} + K(\Delta l_M),$$

wherein $\Delta l_M$ is the change in l between any measurement of l, and the measurement of l when the skull expansion was approximately zero.

11. A method according to claim 10 wherein each of said steps of monitoring said skull expansion and measuring said change $\Delta l$ comprises the steps of:
    coupling an acoustic signal to a first location on the patient's skin adjacent the skull of the patient;
    detecting said acoustic signal at a second location on the patient's skin adjacent the skull of the patient; and
    measuring a phase difference between said acoustic signal so-coupled at said first location and said acoustic signal so-detected at said second location, wherein said phase difference is indicative of said change $\Delta l$.

12. A method according to claim 11 further comprising the step of applying pressure to the patient's skin at each of said first location and said second location prior to said steps of coupling and detecting, wherein pulsatile blood perfusion at said first location and said second location is reduced.

13. A method according to claim 11 wherein said first location and said second location are approximately diametrically-opposed to one another on either side of the skull of the patient.

14. A method according to claim 11 wherein said first location and said second location are approximately the same location.

15. A method according to claim 10 wherein said step of inducing comprises the step of manipulating the patient in a mechanical fashion.

16. A method according to claim 10 wherein said step of inducing comprises the step of manipulating the patient in a chemical fashion.

17. A method according to claim 10 wherein said step of causing comprises the step of manipulating the patient in a mechancal fashion.

18. A method according to claim 10 wherein said step of causing comprises the step of manipulating the patient in a chemical fashion.

19. A method of determining absolute ICP in a patient, comprising the steps of:
    coupling an acoustic signal to a first location on the patient's skin adjacent the skull of the patient;
    detecting said acoustic signal at a second location on the patient's skin adjacent the skull of the patient;
    measuring a phase difference between said acoustic signal so-coupled at said first location and said acoustic signal so-detected at said second location, wherein said phase difference is indicative of skull expansion of the patient;
    repeating said steps of coupling, detecting, and measuring for a period of time;
    inducing changes in ICP in the patient during said period of time;
    determining a time during said time period when said phase difference is approximately zero;
    measuring blood pressure of the patient at said time, wherein said blood pressure at said time is indicative of a reference ICP value;
    causing a known change in ICP in the patient after said time;
    measuring a change in said skull expansion of the patient associated with said known change in ICP; and
    determining a skull expansion calibration factor, wherein the absolute ICP is a function of said reference ICP value, said measured change in skull expansion, and said skull expansion calibration factor.

20. A method according to claim 19 further comprising the step of applying pressure to the patient's skin at each of said first location and said second location prior to said steps of coupling and detecting, wherein pulsatile blood perfusion at said first location and said second location is reduced.

21. A method according to claim 19 wherein said first location and said second location are approximately diametrically-opposed to one another on either side of the skull of the patient.

22. A method according to claim 19 wherein said first location and said second location are approximately the same location.

23. A method according to claim 19 wherein said step of inducing comprises the step of manipulating the patient in a mechanical fashion.

24. A method according to claim 19 wherein said step of inducing comprises the step of manipulating the patient in a chemical fashion.

25. A method according to claim 19 wherein said step of causing comprises the step of manipulating the patient in a mechanical fashion.

26. A method according to claim 19 wherein said step of causing comprises the step of manipulating the patient in a chemical fashion.

27. A method of determining absolute ICP in a patient, comprising steps for:

monitoring skull expansion;

inducing changes in ICP;

determining a reference ICP; and determining a skull expansion calibration factor, wherein absolute ICP is a function of said reference ICP, said skull expansion factor, and a measured change in skull dimension.

28. A method according to claim 27, wherein said step for determining a reference ICP comprises the step of measuring blood pressure corresponding to a time when skull expansion equals approximately zero during said step for inducing.

29. A method of claim 27 wherein said step for determining a skull expansion calibration factor comprises the steps of:

causing a known change in ICP in the patient; and measuring the change in skull expansion associated with said known change in ICP.

30. A method according to claim 29 wherein each of said steps for monitoring skull expansion and measuring said change in skull expansion comprises the steps of:

coupling an acoustic signal to a first location on the patient's skin adjacent the skull of the patient;

detecting said acoustic signal at a second location on the patient's skin adjacent the skull of the patient; and measuring phase differences between said acoustic signal so-coupled at said first location and said acoustic signal so-detected at said second location, wherein said phase differences are indicative of said skull expansion.

31. A method according to claim 30 further comprising the step of applying pressure to the patient's skin at each of said first location and said second location prior to said steps of coupling and detecting, wherein pulsatile blood perfusion at said first location and said second location is reduced.

32. A method according to claim 30 wherein said first location and said second location are approximately diametrically-opposed to one another on either side of the skull of the patient.

33. A method according to claim 30 wherein said first location and said second location are approximately the same location.

34. A method according to claim 27 wherein said step for inducing comprises the step of manipulating the patient in a mechanical fashion.

35. A method according to claim 27 wherein said step for inducing comprises the step of manipulating the patient in a chemical fashion.

36. A method according to claim 29 wherein said step for causing comprises the step of manipulating the patient in a mechanical fashion.

37. A method according to claim 29 wherein said step for causing comprises the step of manipulating the patient in a chemical fashion.

* * * * *

UNITED STATES PATENT AND TRADEMARK OFFICE
CERTIFICATE OF CORRECTION

PATENT NO.    : 6,773,407 B2
DATED         : August 10, 2004
INVENTOR(S)   : William T. Yost, John H. Cantrell, Jr. and Alan R. Hargens It is certified that error appears in the above-identified patent and that said Letters Patent is hereby corrected as shown below:

Title page,
Item [75], Inventors, replace "Alan E. Hargens, San Diego, CA (US)" with
-- Alan R. Hargens, San Diego, CA (US) --

Signed and Sealed this

Eighth Day of February, 2005

JON W. DUDAS
*Director of the United States Patent and Trademark Office*